(12) United States Patent
Marci et al.

(10) Patent No.: US 9,292,858 B2
(45) Date of Patent: *Mar. 22, 2016

(54) DATA COLLECTION SYSTEM FOR AGGREGATING BIOLOGICALLY BASED MEASURES IN ASYNCHRONOUS GEOGRAPHICALLY DISTRIBUTED PUBLIC ENVIRONMENTS

(75) Inventors: Carl D. Marci, Boston, MA (US); Brian Levine, Needham, MA (US); Ravi Kanth V Kothuri, Nashua, NH (US); Geoff Gill, Newton, MA (US)

(73) Assignee: THE NIELSEN COMPANY (US), LLC, New York, NY (US)

( * ) Notice: Subject to any disclaimer, the term of this patent is extended or adjusted under 35 U.S.C. 154(b) by 513 days.

This patent is subject to a terminal disclaimer.

(21) Appl. No.: 13/405,611

(22) Filed: Feb. 27, 2012

(65) Prior Publication Data

US 2013/0226464 A1 Aug. 29, 2013

(51) Int. Cl.
| | |
|---|---|
| *G06Q 10/00* | (2012.01) |
| *G06Q 30/00* | (2012.01) |
| *G06Q 30/02* | (2012.01) |
| *A61B 5/16* | (2006.01) |
| *A61B 5/00* | (2006.01) |
| *A61B 5/024* | (2006.01) |
| *A61B 5/0476* | (2006.01) |

(Continued)

(52) U.S. Cl.
CPC ............. *G06Q 30/0201* (2013.01); *A61B 5/16* (2013.01); *A61B 5/0002* (2013.01); *A61B 5/02405* (2013.01); *A61B 5/0476* (2013.01); *A61B 5/0533* (2013.01); *A61B 5/08* (2013.01); *A61B 5/11* (2013.01); *A61B 5/225* (2013.01); *A61B 5/6897* (2013.01); *H04H 60/33* (2013.01)

(58) Field of Classification Search
CPC ............. G06Q 30/0201; A61B 5/0002; A61B 5/02405; A61B 5/0476; A61B 5/0533; A61B 5/08; A61B 5/11; A61B 5/16; A61B 5/225; A61B 5/6897; H04H 60/33
USPC ........................................................ 705/7.29
See application file for complete search history.

(56) References Cited

U.S. PATENT DOCUMENTS

| | | |
|---|---|---|
| 2,549,836 A | 4/1951 | McIntyre et al. |
| 3,490,439 A | 1/1970 | Rolston |

(Continued)

FOREIGN PATENT DOCUMENTS

| | | |
|---|---|---|
| DE | 10 2010 005 551 | 7/2011 |
| DE | 10 2010 017 415 | 12/2011 |

(Continued)

OTHER PUBLICATIONS

Watching Ads Is Real Science Research Companies Monitor Physiological Reactions to Commercials to Determine Their Effectiveness.: [3 Star Edition] Bruce Horvitz Los Angeles Times. Orlando Sentinel [Orlando, Fla] Sep. 1, 1991: D1.*

(Continued)

*Primary Examiner* — Timothy Padot
(74) *Attorney, Agent, or Firm* — Hanley, Flight & Zimmerman LLC (57) ABSTRACT

The present invention relates to biologically and behaviorally based systems and methods for measuring audience response to a target stimulus. The systems and methods are deployable in multiple locations and may display stimuli based on location, target demographics, and combinations thereof.

19 Claims, 1 Drawing Sheet

(51) Int. Cl.
  *A61B 5/053* (2006.01)
  *A61B 5/08* (2006.01)
  *A61B 5/11* (2006.01)
  *A61B 5/22* (2006.01)
  *H04H 60/33* (2008.01)

(56) References Cited

U.S. PATENT DOCUMENTS

| | | |
|---|---|---|
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,870,579 A | 9/1989 | Hey .................. 705/7.31 |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,024,235 A | 6/1991 | Ayers |
| 5,038,782 A | 8/1991 | Gevins et al. |
| 5,052,401 A | 10/1991 | Sherwin |
| 5,083,571 A | 1/1992 | Prichep |
| 5,137,027 A | 8/1992 | Rosenfeld |
| 5,243,517 A | 9/1993 | Schmidt et al. ............ 364/419.2 |
| 5,273,037 A | 12/1993 | Itil et al. |
| 5,291,888 A | 3/1994 | Tucker |
| 5,295,491 A | 3/1994 | Gevins |
| 5,339,826 A | 8/1994 | Schmidt et al. |
| 5,345,281 A | 9/1994 | Taboada et al. |
| 5,357,957 A | 10/1994 | Itil et al. |
| 5,392,788 A | 2/1995 | Hudspeth |
| 5,406,956 A | 4/1995 | Farwell |
| 5,436,830 A | 7/1995 | Zaltman .................. 364/419.2 |
| 5,447,166 A | 9/1995 | Gevins |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,617,855 A | 4/1997 | Waletzky et al. |
| 5,649,061 A | 7/1997 | Smyth |
| 5,655,534 A | 8/1997 | Ilmoniemi |
| 5,676,138 A | 10/1997 | Zawilinski |
| 5,676,148 A | 10/1997 | Koo et al. ............ 128/661.01 |
| 5,720,619 A | 2/1998 | Fisslinger |
| 5,724,987 A | 3/1998 | Gevins et al. |
| 5,736,986 A | 4/1998 | Sever, Jr. |
| 5,762,611 A | 6/1998 | Lewis et al. |
| 5,771,897 A | 6/1998 | Zufrin |
| 5,774,591 A | 6/1998 | Black et al. |
| 5,800,351 A | 9/1998 | Mann |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. .................. 1/1 |
| 5,892,566 A | 4/1999 | Bullwinkel |
| 5,961,332 A | 10/1999 | Joao |
| 5,983,129 A | 11/1999 | Cowan et al. |
| 5,995,868 A | 11/1999 | Dorfmeister et al. |
| 6,001,065 A | 12/1999 | DeVito |
| 6,016,444 A | 1/2000 | John |
| 6,021,346 A | 2/2000 | Ryu et al. |
| 6,052,619 A | 4/2000 | John |
| 6,088,040 A | 7/2000 | Oda et al. |
| 6,099,319 A | 8/2000 | Zaltman et al. |
| 6,117,092 A | 9/2000 | Weinstein et al. |
| 6,120,440 A | 9/2000 | Goknar |
| 6,154,669 A | 11/2000 | Hunter et al. |
| 6,161,030 A | 12/2000 | Levendowski et al. |
| 6,171,239 B1 | 1/2001 | Humphrey |
| 6,175,753 B1 | 1/2001 | Menkes et al. |
| 6,212,502 B1 | 4/2001 | Ball et al. |
| 6,228,038 B1 | 5/2001 | Claessens |
| 6,254,536 B1 | 7/2001 | DeVito |
| 6,259,889 B1 | 7/2001 | LeDue |
| 6,270,466 B1 | 8/2001 | Weinstein et al. |
| 6,286,005 B1 | 9/2001 | Cannon |
| 6,289,234 B1 | 9/2001 | Mueller |
| 6,292,688 B1 * | 9/2001 | Patton .................. A61B 5/16 600/300 |
| 6,299,308 B1 | 10/2001 | Voronka et al. |
| 6,301,493 B1 | 10/2001 | Marro et al. |
| 6,315,569 B1 | 11/2001 | Zaltman .................. 434/236 |
| 6,330,470 B1 | 12/2001 | Tucker et al. |
| 6,334,778 B1 | 1/2002 | Brown |
| 6,349,231 B1 | 2/2002 | Musha |
| 6,358,201 B1 | 3/2002 | Childre et al. .................. 600/300 |
| 6,374,143 B1 | 4/2002 | Berrang et al. |
| 6,422,999 B1 * | 7/2002 | Hill .................. A61B 5/0488 600/300 |
| 6,425,764 B1 | 7/2002 | Lamson |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett et al. |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,575,902 B1 | 6/2003 | Burton |
| 6,577,329 B1 | 6/2003 | Flickner et al. |
| 6,585,521 B1 | 7/2003 | Obrador |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,688,890 B2 | 2/2004 | von Buegner |
| 6,699,188 B2 | 3/2004 | Wessel |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |
| 6,792,304 B1 | 9/2004 | Silberstein |
| 6,842,877 B2 | 1/2005 | Robarts et al. |
| 6,850,252 B1 | 2/2005 | Hoffberg .................. 345/716 |
| 6,852,875 B2 | 2/2005 | Prakash .................. 560/40 |
| 6,888,457 B2 | 5/2005 | Wilkinson et al. ............ 340/540 |
| 6,904,408 B1 | 6/2005 | McCarthy et al. |
| 6,950,698 B2 | 9/2005 | Sarkela et al. |
| 6,993,380 B1 | 1/2006 | Modarres |
| 7,120,880 B1 | 10/2006 | Dryer et al. |
| 7,127,283 B2 | 10/2006 | Kageyama |
| 7,130,673 B2 | 10/2006 | Tolvanen-Laakso et al. |
| 7,150,715 B2 | 12/2006 | Collura et al. |
| 7,177,675 B2 | 2/2007 | Suffin et al. |
| 7,194,186 B1 | 3/2007 | Strub et al. |
| 7,246,081 B2 | 7/2007 | Hill |
| 7,340,060 B2 | 3/2008 | Tomkins et al. |
| 7,383,728 B2 | 6/2008 | Noble et al. |
| 7,496,400 B2 | 2/2009 | Hoskonen et al. |
| 7,548,774 B2 | 6/2009 | Kurtz et al. |

(56) References Cited

U.S. PATENT DOCUMENTS

| | | |
|---|---|---|
| 7,551,952 B2 | 6/2009 | Gevins et al. |
| 7,627,880 B2 | 12/2009 | Itakura |
| 7,630,757 B2 | 12/2009 | Dorfmeister et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,716,697 B2 | 5/2010 | Morikawa et al. |
| 7,729,755 B2 | 6/2010 | Laken |
| 7,739,140 B2 | 6/2010 | Vinson et al. |
| 7,742,623 B1 | 6/2010 | Moon et al. |
| 7,751,878 B1 | 7/2010 | Merkle et al. |
| 7,797,186 B2 | 9/2010 | Dybus ............................ 705/10 |
| 7,805,009 B2 | 9/2010 | Everett et al. |
| 7,840,248 B2 | 11/2010 | Fuchs et al. |
| 7,840,250 B2 | 11/2010 | Tucker |
| 7,853,122 B2 | 12/2010 | Miura et al. |
| 7,930,199 B1 | 4/2011 | Hill ............................ 705/7.29 |
| 7,942,816 B2 | 5/2011 | Satoh et al. |
| 8,014,847 B2 | 9/2011 | Shastri et al. |
| 8,027,518 B2 | 9/2011 | Baker et al. |
| 8,055,722 B2 | 11/2011 | Hille |
| 8,069,125 B2 | 11/2011 | Jung et al. |
| 8,082,215 B2 | 12/2011 | Jung et al. |
| 8,086,563 B2 | 12/2011 | Jung et al. |
| 8,103,328 B2 | 1/2012 | Turner et al. |
| 8,165,916 B2 | 4/2012 | Hoffberg et al. |
| 8,209,224 B2 | 6/2012 | Pradeep et al. |
| 8,235,725 B1 | 8/2012 | Hill |
| 8,239,030 B1 | 8/2012 | Hagedorn et al. |
| 8,255,267 B2 | 8/2012 | Breiter |
| 8,327,395 B2 | 12/2012 | Lee |
| 8,332,883 B2 | 12/2012 | Lee |
| 8,335,715 B2 | 12/2012 | Pradeep et al. |
| 8,386,312 B2 | 2/2013 | Pradeep et al. |
| 8,386,313 B2 | 2/2013 | Pradeep et al. |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,473,345 B2 | 6/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,548,852 B2 | 10/2013 | Pradeep et al. |
| 8,600,100 B2 | 12/2013 | Hill |
| 8,655,428 B2 | 2/2014 | Pradeep et al. |
| 8,655,437 B2 | 2/2014 | Pradeep et al. |
| 8,793,715 B1 | 7/2014 | Weitzenfeld et al. |
| 2001/0013009 A1 | 8/2001 | Greening et al. |
| 2001/0056225 A1 | 12/2001 | DeVito |
| 2002/0059577 A1 | 5/2002 | Lu et al. |
| 2002/0072952 A1 | 6/2002 | Hamzey et al. |
| 2002/0077534 A1 | 6/2002 | DuRousseau |
| 2002/0103429 A1 | 8/2002 | deCharms |
| 2002/0107454 A1 | 8/2002 | Collura et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0055355 A1 | 3/2003 | Vieritio-Oja |
| 2003/0059750 A1 | 3/2003 | Bindler et al. |
| 2003/0063222 A1 | 4/2003 | Creed et al. |
| 2003/0065524 A1 | 4/2003 | Giacchetti et al. |
| 2003/0066071 A1 | 4/2003 | Gutta et al. |
| 2003/0067486 A1 | 4/2003 | Lee et al. |
| 2003/0073921 A1 | 4/2003 | Sohmer et al. |
| 2003/0081834 A1 | 5/2003 | Philomin et al. |
| 2003/0093792 A1 | 5/2003 | Labeeb et al. |
| 2003/0100998 A2 | 5/2003 | Brunner et al. |
| 2003/0149344 A1 | 8/2003 | Nizan |
| 2003/0165270 A1 | 9/2003 | Endrikhovski et al. |
| 2003/0208754 A1 | 11/2003 | Sridhar et al. |
| 2004/0005143 A1 | 1/2004 | Tsuru et al. |
| 2004/0013398 A1 | 1/2004 | Miura et al. |
| 2004/0073129 A1 | 4/2004 | Caldwell et al. |
| 2004/0077934 A1 | 4/2004 | Massad |
| 2004/0092809 A1 | 5/2004 | DeCharms |
| 2004/0098298 A1 | 5/2004 | Yin |
| 2004/0111033 A1 | 6/2004 | Oung et al. |
| 2004/0133081 A1 | 7/2004 | Teller et al. |
| 2004/0161730 A1 | 8/2004 | Urman |
| 2004/0187167 A1 | 9/2004 | Maguire et al. |
| 2004/0193068 A1 | 9/2004 | Burton et al. |
| 2004/0210159 A1 | 10/2004 | Kibar et al. |
| 2004/0219184 A1 | 11/2004 | Brown et al. |
| 2004/0220483 A1 | 11/2004 | Yeo et al. |
| 2005/0010116 A1 | 1/2005 | Korhonen et al. |
| 2005/0060312 A1 | 3/2005 | Curtiss et al. |
| 2005/0062637 A1 | 3/2005 | El Zabadani et al. |
| 2005/0071462 A1 | 3/2005 | Bodin et al. |
| 2005/0071865 A1 | 3/2005 | Martins |
| 2005/0079474 A1 | 4/2005 | Lowe |
| 2005/0107716 A1 | 5/2005 | Eaton et al. |
| 2005/0143629 A1 | 6/2005 | Farwell |
| 2005/0154290 A1 | 7/2005 | Langleben |
| 2005/0177058 A1 | 8/2005 | Sobell |
| 2005/0197590 A1 | 9/2005 | Osorio et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0273017 A1 | 12/2005 | Gordon |
| 2005/0288954 A1 | 12/2005 | McCarthy et al. |
| 2005/0289582 A1 | 12/2005 | Tavares et al. |
| 2006/0010470 A1 | 1/2006 | Kurosaki et al. |
| 2006/0041548 A1* | 2/2006 | Parsons .................. G06Q 30/02 |
| 2006/0064037 A1 | 3/2006 | Shalon et al. |
| 2006/0094970 A1 | 5/2006 | Drew |
| 2006/0094971 A1 | 5/2006 | Drew |
| 2006/0111621 A1 | 5/2006 | Coppi et al. |
| 2006/0111644 A1 | 5/2006 | Guttag et al. |
| 2006/0129458 A1 | 6/2006 | Maggio |
| 2006/0143647 A1 | 6/2006 | Bill |
| 2006/0149337 A1 | 7/2006 | John |
| 2006/0167376 A1 | 7/2006 | Viirre et al. |
| 2006/0190822 A1 | 8/2006 | Basson et al. |
| 2006/0217598 A1 | 9/2006 | Miyajima et al. |
| 2006/0256133 A1 | 11/2006 | Rosenberg |
| 2006/0257834 A1 | 11/2006 | Lee et al. |
| 2006/0258926 A1 | 11/2006 | Ali et al. |
| 2006/0259360 A1 | 11/2006 | Flinn et al. |
| 2006/0265022 A1 | 11/2006 | John et al. |
| 2006/0293608 A1 | 12/2006 | Rothman et al. |
| 2006/0293921 A1 | 12/2006 | McCarthy et al. |
| 2007/0016096 A1 | 1/2007 | McNabb |
| 2007/0038516 A1 | 2/2007 | Apple et al. |
| 2007/0048707 A1 | 3/2007 | Caamano et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066914 A1 | 3/2007 | Le et al. |
| 2007/0066915 A1 | 3/2007 | Frei et al. |
| 2007/0066916 A1 | 3/2007 | Lemos |
| 2007/0106170 A1 | 5/2007 | Dunseath, Jr. et al. |
| 2007/0135727 A1 | 6/2007 | Virtanen et al. |
| 2007/0135728 A1 | 6/2007 | Snyder et al. |
| 2007/0150916 A1 | 6/2007 | Begole et al. |
| 2007/0173733 A1 | 7/2007 | Le et al. |
| 2007/0225585 A1 | 9/2007 | Washbon et al. |
| 2007/0225674 A1 | 9/2007 | Molnar et al. |
| 2007/0235716 A1 | 10/2007 | Delic et al. |
| 2007/0238945 A1 | 10/2007 | Delic et al. |
| 2007/0249952 A1 | 10/2007 | Rubin et al. |
| 2007/0250901 A1 | 10/2007 | McIntire et al. |
| 2007/0265507 A1 | 11/2007 | de Lemos |
| 2007/0282566 A1 | 12/2007 | Whitlow et al. |
| 2008/0001600 A1 | 1/2008 | deCharms |
| 2008/0027345 A1 | 1/2008 | Kumada et al. |
| 2008/0039737 A1 | 2/2008 | Breiter et al. |
| 2008/0065468 A1 | 3/2008 | Berg et al. |
| 2008/0081961 A1 | 4/2008 | Westbrook et al. |
| 2008/0082019 A1 | 4/2008 | Ludving et al. |

(56) References Cited

U.S. PATENT DOCUMENTS

| | | | |
|---|---|---|---|
| 2008/0091512 A1* | 4/2008 | Marci | G06Q 30/0242 705/7.29 |
| 2008/0097854 A1 | 4/2008 | Young | |
| 2008/0144882 A1 | 6/2008 | Leinbach et al. | |
| 2008/0147488 A1 | 6/2008 | Tunick et al. | |
| 2008/0147742 A1 | 6/2008 | Allen | |
| 2008/0159365 A1 | 7/2008 | Dubocanin et al. | |
| 2008/0162182 A1 | 7/2008 | Cazares et al. | |
| 2008/0177197 A1 | 7/2008 | Lee et al. | |
| 2008/0208072 A1 | 8/2008 | Fadem et al. | |
| 2008/0214902 A1 | 9/2008 | Lee et al. | |
| 2008/0218472 A1 | 9/2008 | Breen et al. | |
| 2008/0221400 A1 | 9/2008 | Lee et al. | |
| 2008/0221472 A1 | 9/2008 | Lee et al. | |
| 2008/0221969 A1 | 9/2008 | Lee et al. | |
| 2008/0222670 A1 | 9/2008 | Lee et al. | |
| 2008/0222671 A1 | 9/2008 | Lee et al. | |
| 2008/0228077 A1 | 9/2008 | Wilk et al. | |
| 2008/0255949 A1 | 10/2008 | Genco et al. | |
| 2008/0295126 A1 | 11/2008 | Lee et al. | |
| 2008/0306398 A1 | 12/2008 | Uchiyama et al. | |
| 2009/0024049 A1 | 1/2009 | Pradeep et al. | |
| 2009/0024447 A1 | 1/2009 | Pradeep et al. | |
| 2009/0024448 A1 | 1/2009 | Pradeep et al. | |
| 2009/0024449 A1 | 1/2009 | Pradeep et al. | |
| 2009/0024475 A1 | 1/2009 | Pradeep et al. | |
| 2009/0025023 A1 | 1/2009 | Pradeep et al. | |
| 2009/0030287 A1 | 1/2009 | Pradeep et al. | |
| 2009/0030303 A1 | 1/2009 | Pradeep et al. | |
| 2009/0030717 A1 | 1/2009 | Pradeep et al. | |
| 2009/0030762 A1 | 1/2009 | Lee et al. | |
| 2009/0030780 A1 | 1/2009 | York et al. | |
| 2009/0030930 A1 | 1/2009 | Pradeep et al. | |
| 2009/0036755 A1 | 2/2009 | Pradeep et al. | |
| 2009/0036756 A1 | 2/2009 | Pradeep et al. | |
| 2009/0062629 A1 | 3/2009 | Pradeep et al. | |
| 2009/0062679 A1 | 3/2009 | Tan et al. | |
| 2009/0062680 A1 | 3/2009 | Sandford | |
| 2009/0062681 A1 | 3/2009 | Pradeep et al. | |
| 2009/0063255 A1 | 3/2009 | Pradeep et al. | |
| 2009/0063256 A1 | 3/2009 | Pradeep et al. | |
| 2009/0070798 A1 | 3/2009 | Lee et al. | |
| 2009/0082643 A1 | 3/2009 | Pradeep et al. | |
| 2009/0082689 A1 | 3/2009 | Guttag et al. | |
| 2009/0083129 A1 | 3/2009 | Pradeep et al. | |
| 2009/0088610 A1 | 4/2009 | Lee et al. | |
| 2009/0094286 A1 | 4/2009 | Lee et al. | |
| 2009/0094627 A1 | 4/2009 | Lee et al. | |
| 2009/0094628 A1 | 4/2009 | Lee et al. | |
| 2009/0094629 A1 | 4/2009 | Lee et al. | |
| 2009/0097689 A1 | 4/2009 | Prest et al. | |
| 2009/0112077 A1 | 4/2009 | Nguyen et al. | |
| 2009/0112117 A1 | 4/2009 | Rewari | |
| 2009/0119154 A1 | 5/2009 | Jung et al. | |
| 2009/0131764 A1 | 5/2009 | Lee et al. | |
| 2009/0132441 A1 | 5/2009 | Muller et al. | |
| 2009/0133047 A1 | 5/2009 | Lee et al. | |
| 2009/0150919 A1 | 6/2009 | Lee et al. | |
| 2009/0156907 A1 | 6/2009 | Jung et al. | |
| 2009/0156955 A1 | 6/2009 | Jung et al. | |
| 2009/0158308 A1 | 6/2009 | Weitzenfeld et al. | |
| 2009/0163777 A1 | 6/2009 | Jung et al. | |
| 2009/0171164 A1 | 7/2009 | Jung et al. | |
| 2009/0187467 A1 | 7/2009 | Fang et al. | |
| 2009/0195392 A1 | 8/2009 | Zalewski | |
| 2009/0214060 A1 | 8/2009 | Chuang et al. | |
| 2009/0248496 A1 | 10/2009 | Hueter et al. | |
| 2009/0248594 A1 | 10/2009 | Castleman et al. | |
| 2009/0253996 A1 | 10/2009 | Lee et al. | |
| 2009/0259137 A1 | 10/2009 | Delic et al. | |
| 2009/0318773 A1 | 12/2009 | Jung et al. | |
| 2009/0318826 A1 | 12/2009 | Green et al. | |
| 2009/0327068 A1 | 12/2009 | Pradeep et al. | |
| 2009/0328089 A1 | 12/2009 | Pradeep et al. | |
| 2010/0004977 A1 | 1/2010 | Marci et al. | |
| 2010/0041962 A1 | 2/2010 | Causevic et al. | |
| 2010/0042012 A1 | 2/2010 | Alhussiny | |
| 2010/0060300 A1 | 3/2010 | Muller et al. | |
| 2010/0076333 A9 | 3/2010 | Burton et al. | |
| 2010/0094702 A1 | 4/2010 | Silberstein et al. | |
| 2010/0125219 A1 | 5/2010 | Harris et al. | |
| 2010/0145176 A1 | 6/2010 | Himes | |
| 2010/0145215 A1 | 6/2010 | Pradeep et al. | |
| 2010/0145217 A1 | 6/2010 | Otto et al. | |
| 2010/0153175 A1 | 6/2010 | Pearson et al. | |
| 2010/0183279 A1 | 7/2010 | Pradeep et al. | |
| 2010/0186031 A1 | 7/2010 | Pradeep et al. | |
| 2010/0186032 A1 | 7/2010 | Pradeep et al. | |
| 2010/0198042 A1 | 8/2010 | Popescu et al. | |
| 2010/0211439 A1 | 8/2010 | Marci et al. | |
| 2010/0214318 A1 | 8/2010 | Pradeep et al. | |
| 2010/0215289 A1 | 8/2010 | Pradeep et al. | |
| 2010/0223094 A1 | 9/2010 | Cumming et al. | |
| 2010/0234752 A1 | 9/2010 | Sullivan et al. | |
| 2010/0249538 A1 | 9/2010 | Pradeep et al. | |
| 2010/0249636 A1 | 9/2010 | Pradeep et al. | |
| 2010/0250325 A1 | 9/2010 | Pradeep et al. | |
| 2010/0274152 A1 | 10/2010 | McPeck et al. | |
| 2010/0274153 A1 | 10/2010 | Tucker et al. | |
| 2010/0317988 A1 | 12/2010 | Terada et al. | |
| 2010/0323716 A1* | 12/2010 | Jaffri | G06Q 30/02 455/456.1 |
| 2010/0331661 A1 | 12/2010 | Nakagawa | |
| 2011/0004089 A1 | 1/2011 | Chou | |
| 2011/0015503 A1 | 1/2011 | Joffe et al. | |
| 2011/0040202 A1 | 2/2011 | Luo et al. | |
| 2011/0046473 A1 | 2/2011 | Pradeep et al. | |
| 2011/0046502 A1 | 2/2011 | Pradeep et al. | |
| 2011/0046503 A1 | 2/2011 | Pradeep et al. | |
| 2011/0046504 A1 | 2/2011 | Pradeep et al. | |
| 2011/0047121 A1 | 2/2011 | Pradeep et al. | |
| 2011/0059422 A1 | 3/2011 | Masaoka | |
| 2011/0084795 A1 | 4/2011 | Fukuyori | |
| 2011/0085700 A1 | 4/2011 | Lee | |
| 2011/0098593 A1 | 4/2011 | Low et al. | |
| 2011/0105937 A1 | 5/2011 | Pradeep et al. | |
| 2011/0106621 A1 | 5/2011 | Pradeep et al. | |
| 2011/0106750 A1 | 5/2011 | Pradeep et al. | |
| 2011/0119124 A1 | 5/2011 | Pradeep et al. | |
| 2011/0119129 A1 | 5/2011 | Pradeep et al. | |
| 2011/0131274 A1 | 6/2011 | Hille | |
| 2011/0144519 A1 | 6/2011 | Causevic | |
| 2011/0161163 A1 | 6/2011 | Carlson et al. | |
| 2011/0224569 A1 | 9/2011 | Isenhart et al. | |
| 2011/0237923 A1 | 9/2011 | Picht et al. | |
| 2011/0237971 A1 | 9/2011 | Pradeep et al. | |
| 2011/0248729 A2 | 10/2011 | Mueller et al. | |
| 2011/0256520 A1 | 10/2011 | Siefert | |
| 2011/0257502 A1 | 10/2011 | Lee | |
| 2011/0257937 A1 | 10/2011 | Lee | |
| 2011/0270620 A1 | 11/2011 | Pradeep et al. | |
| 2011/0276504 A1 | 11/2011 | Pradeep et al. | |
| 2011/0282231 A1 | 11/2011 | Pradeep et al. | |
| 2011/0282232 A1 | 11/2011 | Pradeep et al. | |
| 2011/0282749 A1 | 11/2011 | Pradeep et al. | |
| 2011/0298706 A1 | 12/2011 | Mann | |
| 2011/0301431 A1 | 12/2011 | Greicius | |
| 2011/0319975 A1 | 12/2011 | Ho et al. | |
| 2012/0002848 A1 | 1/2012 | Hill | |
| 2012/0022391 A1 | 1/2012 | Leuthardt | |
| 2012/0036004 A1 | 2/2012 | Pradeep et al. | |
| 2012/0036005 A1 | 2/2012 | Pradeep et al. | |
| 2012/0046993 A1 | 2/2012 | Hill | |
| 2012/0054018 A1 | 3/2012 | Pradeep et al. | |
| 2012/0072289 A1 | 3/2012 | Pradeep et al. | |
| 2012/0072939 A1 | 3/2012 | Crenshaw | |
| 2012/0089552 A1 | 4/2012 | Chang et al. | |
| 2012/0108995 A1 | 5/2012 | Pradeep et al. | |
| 2012/0130800 A1 | 5/2012 | Pradeep et al. | |
| 2012/0203640 A1* | 8/2012 | Karmarkar | G06F 1/1686 705/14.66 |
| 2012/0249797 A1 | 10/2012 | Haddick et al. | |
| 2012/0254909 A1 | 10/2012 | Serdiuk | |
| 2012/0289794 A1 | 11/2012 | Jain et al. | |

(56) References Cited

U.S. PATENT DOCUMENTS

| | | |
|---|---|---|
| 2013/0024272 A1 | 1/2013 | Pradeep et al. |
| 2013/0060125 A1 | 3/2013 | Zeman |
| 2013/0094722 A1 | 4/2013 | Hill |
| 2013/0121591 A1 | 5/2013 | Hill |
| 2013/0166373 A1 | 6/2013 | Pradeep et al. |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0304540 A1 | 11/2013 | Pradeep et al. |
| 2013/0311132 A1 | 11/2013 | Tobita |
| 2013/0332259 A1 | 12/2013 | Pradeep et al. |
| 2014/0025620 A1 | 1/2014 | Greenzeiger et al. |
| 2014/0039857 A1 | 2/2014 | Hill |
| 2014/0039975 A1 | 2/2014 | Hill |
| 2014/0162225 A1 | 6/2014 | Hill |

FOREIGN PATENT DOCUMENTS

| | | |
|---|---|---|
| GB | 1374658 | 11/1974 |
| GB | 2221759 | 2/1990 |
| JP | 05-293172 | 11/1993 |
| JP | 2001-147944 | 5/2001 |
| JP | 2002-000577 | 1/2002 |
| JP | 2002056500 | 2/2002 |
| JP | 2002-344904 | 11/2002 |
| JP | 2003-111106 | 4/2003 |
| JP | 2003-178078 | 6/2003 |
| JP | 2003522580 | 7/2003 |
| JP | 2005-51654 | 2/2005 |
| JP | 2006-227994 | 8/2006 |
| JP | 2006-323547 | 11/2006 |
| JP | 2006-6355 | 7/2007 |
| WO | 95-18565 | 7/1995 |
| WO | 97-17774 | 5/1997 |
| WO | 97-40745 | 11/1997 |
| WO | 97-41673 | 11/1997 |
| WO | 00/17827 | 3/2000 |
| WO | 02-100241 | 12/2002 |
| WO | 02-102238 | 12/2002 |
| WO | 2004/100765 | 11/2004 |
| WO | 2006/005767 | 1/2006 |
| WO | 2007/019584 | 2/2007 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |
| WO | 2011-062795 | 5/2011 |

OTHER PUBLICATIONS

Multi-Platform Messaging: The Medium Matters. Treutler, Theresa; Levine, Brian; Marci, Carl D. Journal of Advertising Research50.3 (2010): 243.*

The Emotional Quotient of Soup Shopping. Iian Brat. The Wall Street Journal. Feb. 17, 2010, p. B6.*

U.S. Appl. No. 12/749,376, filed Mar. 29, 2010.

U.S. Appl. No. 13/089,752, filed Apr. 19, 2011.

International Search Report dated Mar. 24, 2008 of International Patent Application No. PCT/US2007/019398.

International Search Report dated Nov. 22, 2011 of International Patent Application No. PCT/US2011/033050.

International Search Report dated Nov. 9, 2010 of International Patent Application No. PCT/US2010/031375.

International Search Report dated Oct. 21, 2010 of International Patent Application No. PCT/US2010/029162.

Non-Final Office Action dated Oct. 18, 2010 of related U.S. Appl. No. 11/850,650.

Final Office Action dated Jun. 8, 2011 of related U.S. Appl. No. 11/850,650.

Non-Final Office Action dated Dec. 13, 2011 of related U.S. Appl. No. 11/850,650.

Non-Final Office Action dated Dec. 21, 2011 of related U.S. Appl. No. 12/749,376.

Australian Office Action dated Mar. 26, 2012 or corresponding Australian Patent Application No. 2007293092.

European Office Action dated Nov. 11, 2011 of corresponding European Patent Application No. 10717912.9.

European Office Action dated Nov. 29, 2011 of corresponding European Patent Application No. 10717932.7.

Japanese Office Action dated Apr. 25, 2012 of corresponding Japanese Patent Application No. 2009-527401.

Canadian Office Action dated Jul. 24, 2014 of related Canadian Patent Application No. 2,662,632.

"ARF, AAAA and ANA Are Getting Emotional about Engagement", Presentation, pp. 1-103 (2005).

Boltz, M.G., "The cognitive processing of film and musical soundtracks", *Memory & Cognition*, 32(7):1194-1205 (2004).

Christie et al., "Autonomic specificity of discrete emotion and dimensions of affective space: a multivariate approach", *Int 'l J. Psychophysiol.*, 51:143-153 (2004).

Coombes et al., "Emotion and movement: Activation of defensive circuitry alters the magnitude of a sustained muscle contraction", *Neurosci. Lett.*, 396:192-196 (2006).

Cryer et al., "Pull the plug on stress", *Harv. Bus. Rev.*, 81(7):102-107 (2003).

Demaree et al., "Predicting facial valence to negative stimuli from resting RSA: Not a function of active emotion regulation", *Cognition and Emotion*, 20(2):161-176 (2006).

Ekman et al., "Autonomic Nervous System Activity Distinguishes among Emotions", *Science*, 221(4616):1208-1210 (1983).

Elton, C., "Measuring emotion at the symphony", http://www.boston.com, pp. 1-3.

Goldberg, C., "Getting wired could help predict emotions", http://www.boston.com, pp. 1-4 (2005).

Gomez et al., "Respiratory responses associated with affective processing of film stimuli", Biol. Psychol., 68:223-235 (2005).

Hall, B.F., "A New Approach to Measuring Advertising Effectiveness", Article 1502a:1-17 (2001).

Hall, B.F., "Advertising as a Factor of production", *Admap*, pp. 30-32 (2003).

Hall, B.F., "Is cognitive processing the right dimension", *Admap*, pp. 37-39 (2003).

Hall, B.F., "On Measuring the Power Communications", *JAR*, pp. 1-11 (2004).

Hall, B.F., "Research and strategy: a fall from grace", *Admap*, pp. 2-4 (2003).

Hall, B.F., "Review of Casting for Big Ideas, by Andrew Jaffe", pp. 1-2 (2003).

Hall, B.F., "Why Advertisers Do It", pp. 1-5 (2003).

Hubert, et al., "Autonomic, neuroendocrine, and subjective responses to emotion-inducing film stimuli", Int'l J. Psychophysiol., 11:131-140 (1991).

Levenson et al., "Emotion and Autonomic Nervous System Activity in the Minangkabau of West Sumatra", *J. Personality Soc. Psychol.*, 62(6):972-988 (1992).

Marci et al., "The Effect of Emotional Distance on Pyschophysiologic Concordance and Perceived Empathy Between Patient and Interviewer", *Appl. Psychophysiol. Biofeedback*, 31:115-129 (2006).

McCraty et al., "Analysis of twenty-four hour heart rate variability in patients with panic disorder", Biol. Psychol., 56(2):131-150 (2001).

McCraty et al., "Electrophysiolocial Evidence of Intuition: Part 1. The Surprising Role of the Heart", J. Altern. Complement. Med., 10(1):133-143 (2004).

McCraty et al., "Electrophysiological Evidence of Intuition: Part 2. A System-Wide Process?", J. Altern. Complement. Med., 10(2\0):325-336 (2004).

(56) References Cited

OTHER PUBLICATIONS

McCraty et al., "Impact of a Workplace Stress Reduction Program on Blood Pressure and Emotional Health in Hypertensive Employees", *J. Altern. Complement. Med.*, 9(3):355-369 (2003).

McCraty et al., "The Effects of Different Types of Music on Mood, Tension, and Mental Clarity", *Altern. Ther. Health Med.*, 4(1):75-84 (1998).

McCraty et al., "The Effects of Emotions on Ahort-Term Power Spectrum Analysis of Heart RateVariability", *Am. J. Cardiol.*, 76(14):1089-1093 (1995).

McCraty et al., "The Impact of a New Emotional Self-Management Program on Stress, Emotions, Heart Rate Variability, DHEA and Cortisol", *Intergr. Physiol. Behav. Sci.*, 33(2):151-170 (1998).

McCraty et al., "The Impact of an Emotional Self-Management Skills Course on Psychosocial Functioning and Autonomic Recovery to Stress in Middle School Children", Integr. Physiol. Behav. Sci., 34(4):246-268 (1999).

Melillo, W., "Inside the consumer mind: What Neuroscience can tell us about marketing", http://www.answerstream.com, pp. 1-13 (2006).

Miller et al., "Influence of Specific Emotional States on Autonomic Reactivity and Pulmonary Function in Asthmatic Children", *J. Am. Acad. Child Adolescent Psychiatry*, 36(5):669-677 (1997).

Murphy et al., "The Heart Reinnervates After Transplantation", *Ann. Thorac. Surg.*, 69(6):1769-1781 (2000).

Ranii, D., "Adding Science to Gut Check", *The News & Observer*, pp. 1 (2005).

Rosenberg, K., "Emotional R.O.I.", *The Hub*, pp. 24-25 (2006).

Tiller et al., "Cardiac Coherence: A New, Noninvasive Measure of Autonomic Nervous System Order", *Altern. Ther. Health Med.*, 2(1):52-65 (1996).

"Topline: Emotional Response to Advertising", *MSW Research*, pp. 1-6 (2005).

Umetani et al., "Twenty-Four Hour Time Domain Heart Rate Variability and Heart Rate: Relations to Age and Gender Over Nine Decades", *J Am. Coll. Cardiol.*, 31(3):593-601 (1998).

Von Leupoldt et al., "Emotions in a Body Plethysmograph", *J Psychophysiol.*, 18(4):170-176 (2004).

Watching Ads Is Real Science Research Companies Monitor Physiological Reactions to Commercials to Determine Their Effectiveness.: [3 Star Edition] Bruce Horovitz Los Angeles Times. Orlando Sentinel [Orlando, Fla] Sep. 1, 1991: D1, 2 pgs.

Wearable feedback systems for rehabilitation Sung, Michael; Marci, Carl; Pentland, Alex. Journal of NeuroEngineering and Rehabilitation 2 (2005), 2 pgs.

One to One Interactive and Innerscope Research Release Preliminary Biomeasures Study Results; Initial Findings Suggest Biomeasures Able to Predict Online Community's Rating of Viral Video Content. PR Newswire [New York] Feb. 28, 2007: n/a.

Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.

Belch et al., "Psychophysiological and Cognitive Response to Sex in Advertising," Advances in Consumer Research, vol. 9, pp. 424-427, (1982), 6 pages.

Berry, Michael J.A. and Linoff, Gordon S., Data Mining Techniques: For Marketing, Sales, and Customer Relationship Management, John Wiley & Sons, Inc., 1997, 672 pages.

Bimler et al., "Categorical perception of facial expressions of emotion: Evidence from multidimensional scaling," Cognition and Emotion, vol. 15(5), pp. 633-658 (Sep. 2001), 26 pages.

Blakeslee, "If You Have a 'Buy Button' in Your Brain, What Pushes It?" The New York Times, www.nytimes.com, (Oct. 19, 2004), 3 pages.

Braeutigam, "Neuroeconomics-From neural systems to economic behavior," Brain Research Bulletin, vol. 67, pp. 355-360, Elsevier, (2005), 6 pages.

Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.

Buschman, et al., "Top-Down Versus Bottom-Up Control of Attention in the Prefrontal and Posterior Parietal Cortices," Science, vol. 315, www.sciencemag.org/cgi/content/full/315/5820/1860, American Association for the Advancement of Science, (Mar. 30, 2007), 4 pages.

Buzsaki, "Neural Syntax: Cell Assemblies, Synapsembles, and Readers," Neuron, vol. 68, Elsevier, (Nov. 4, 2010), 24 pages.

Canolty, et al., "High Gamma Power Is Phase-Locked to Theta Oscillations in Human Neocortex," Science, vol. 313, www.sciencemag.org, (Sep. 15, 2006), 3 pages.

Canolty, et al., "The functional role of cross-frequency coupling," Trends in Cognitive Sciences, Elsevier, (Nov. 2010) 11 pages.

Chang, et al., "Categorical speech representation in human superior temporal gyrus," Nature Neuroscience, doi: 10.1038/nn.2641, (Oct. 3, 2010), 6 pages.

Cheng, et al. "Gender Differences in the Mu Rhythm of the Human Mirror-Neuron System," PLos ONE, vol. 3, Issue 5, www.plosone.org, (May 2008), 7 pages.

Coan, J. A, et al., "Voluntary Facial Expression and Hemispheric Asymmetry Over the Frontal Cortex," Psychophysiology, 38 (Nov. 2001), pp. 912-925, 14 pages.

Cohn et al., "Active Learning with Statistical Models," Journal of Artificial Intelligence Research 4, A1 Access Foundation and Morgan Kaufmann Publishers, USA, 1996, 17 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

D'Esposito, "From cognitive to neural models of working memory," Phil. Trans. R. Soc. B, doi: 10.1098/rstb.2007.2086, (Mar. 30, 2007), 12 pages.

Davidson, et al., "The functional neuroanatomy of emotion and affective style," Trends in Cognitive Sciences, vol. 3, No. 1, (Jan. 1999), 11 pages.

de Gelder et al., "Categorical Perception of Facial Expressions: Categories and their Internal Structure," Cognition and Emotion, vol. 11(1), pp. 1-23 (1997), 23 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Dien, et al., "Application of Repeated Measures ANOVA to High-Density Datasets: A Review and Tutorial," in Event-Related Potentials: A Methods Handbook pp. 57-82, (Todd C. Handy, ed., 2005), 14 pages.

Edgar, et al., "Digital Filters in ERP Research," in Event-Related Potentials: A Methods Handbook pp. 85-113, (Todd C. Handy, ed., 2005), 15 pages.

EEG Protocols, "Protocols for EEG Recording," retrieved from the Internet on Aug. 23, 2011, http://www.q-metrx.com/EEGrecordingProtocols.pdf, (Nov. 13, 2007), 3 pages.

Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.

Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.

European Office Action dated Mar. 14, 2013 of corresponding European Patent Application No. 10717912.9, 20 pages.

European Office Action dated Nov. 29, 2011 of corresponding European Patent Application No. 10717932.7, 2 pages.

European Supplementary Search Report dated Mar. 1, 2013 of corresponding European Patent Application No. 10717912.9, 2 pages.

Filler, "MR Neurography and Diffusion Tensor Imaging: Origins, History & Clinical Impact of the first 50,000 Cases With an Assortment of Efficacy and Utility in a Prospective 5,000 Patient Study Group," Institute for Nerve Medicine, (Nov. 7, 2008), 56 pages.

(56) References Cited

OTHER PUBLICATIONS

Final Office Action dated Dec. 19, 2012 of related U.S. Appl. No. 12/426,259, 22 pages.
Final Office Action dated Feb. 27, 2015 of related U.S. Appl. No. 13/779,528, 14 pages.
Final Office Action dated Oct. 4, 2012 of related U.S. Appl. No. 12/749,376, 24 pages.
Flinker, A. et al, "Sub-centimeter language organization in the human temporal lobe," Brain and Language, Elsevier Inc., (2010), doi.org/10.1016/j.bandl.2010.09.009, 7 pages.
Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.
Friedman, et al., "Event-Related Potential (ERP) Studies of Memory Encoding and Retrieval: A Selective Review," Microscopy Research and Technique 51:6-28, Wiley-Less, Inc. (2000), 23 pages.
Fries, "A mechanism for cognitive dynamics: neuronal communication through neuronal coherence," Trends in Cognitive Sciences, vol. 9, No. 10, pp. 474-480, Elsevier B.V. www.sciencedirect.com, (Oct. 2005), 7 pages.
Fuster, "Cortex and Memory: Emergence of a New Paradigm," Journal of Cognitive Neuroscience, vol. 21, No. 11, pp. 2047-2072, Massachusetts Institute of Technology, (Nov. 2009), 26 pages.
Gaillard, "Problems and Paradigms in ERP Research," Biological Psychology, Elsevier Science Publisher B.V. (1988), 10 pages.
Gargiulo et al., "A Mobile EEG System With Dry Electrodes," (Nov. 2008), 4 pages.
Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.
Grefenstette et al., "Validating the Coverage of Lexical Resources for Affect Analysis and Automatically Classifying New Words along Semantic Axes," Chapter X, 3, Mar. 2004, 16 pages.
Griss et al., "Characterization of micromachined spiked biopotential electrodes", Biomedical Engineering, IEEE Transactions, vol. 49, No. 6, (Jun. 2002), 8 pages.
Han, Micheline Kamber Jiawei, Data Mining: Concepts and Techniques, Second Edition (The Morgan Kaufmann Series in Data Management Systems), Elsevier, Inc., 2006, 772 pages.
Haq, "This Is Your Brain on Advertising," BusinessWeek, Market Research, (Oct. 8, 2007), 4 pages.
Hartikainen et al., Manuscript Draft of "Emotionally arousing stimuli compete with attention to left hemispace," NeuroReport, (Sep. 8, 2007), 26 pages.
Hazlett, et al., "Emotional Response to Television Commercials: Facial EMG vs. Self-Report," Journal of Advertising Research, (Apr. 1999), 17 pages.
Herrmann, et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.
Hopf, et al., "Neural Sources of Focused Attention in Visual Search," Cerebral Cortex, 10:1233-1241, Oxford University Press, (Dec. 2000), 9 pages.
Japanese Office Action dated Apr. 23, 2012 of corresponding Japanese Patent Application No. 2009-527401, 16 pages.
Jung et al., "Analysis and Visualization of Single-Trial Event-Related Potentials," Human Brain Mapping vol. 14, 166-185 (2001), 20 pages.
Kay et al., "Identifying natural images from human brain activity," Nature, vol. 452, pp. 352-356, Nature Publishing Group, (Mar. 20, 2008), 5 pages.
Keren, et al., "Saccadic spike potentials in gamma-band EEG: Characterization, detection and suppression," NeuroImage, http://dx.doi:10.1016/j.neuroimage.2009.10.057, (Oct. 2009), 16 pages.
Kishiyama, et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Kishiyama, et al., "Socioeconomic Disparities Affect Prefrontal Function in Children," Journal of Cognitive Neuroscience pp. 1106-1115, Massachusetts Institute of Technology, (2008), 10 pages.
Klimesch, "EEG alpha and theta oscillations reflect cognitive and memory performance a review and analysis," Brain Research Reviews, vol. 29, 169-195, (1999), 27 pages.
Yap et al., "TIMER: Tensor Image Morphing for Elastic Registration," NeuroImage, vol. 47, (May 3, 2009), 15 pages.
Yuval-Greenberg, et al., "Transient Induced Gamma-Band Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 9 pages.
Aaker et al., "Warmth in Advertising: Measurement, Impact, and Sequence Effects," Journal of Consumer Research, vol. 12, No. 4, pp. 365-381, (Mar. 1986), 18 pages.
Akam, et al., "Oscillations and Filtering Networks Support Flexible Routing of Information," Neuron, vol. 67, pp. 308-320, Elsevier, (Jul. 29, 2010), 13 pages.
Allen et al., "A Method of Removing Imaging Artifact from Continuous EEG Recorded during Functional MRI," Neuroimage, vol. 12, 230-239, (Aug. 2000), 12 pages.
Ambler et al., "Ads on the Brain: A Neuro-Imaging Comparison of Cognitive and Affective Advertising Stimuli," London Business School, Centre for Marketing Working Paper, No. 00-902, (Mar. 2000), 23 pages.
Ambler, "Salience and Choice: Neural Correlates of Shopping Decisions," Psychology & Marketing, vol. 21, No. 4, pp. 247-261, Wiley Periodicals, Inc., doi: 10.1002/mar20004, (Apr. 2004), 16 pages.
Arousal in Sport, in Encyclopedia of Applied Psychology, vol. 1, p. 159, retrieved from Google Books, (Spielberger, ed., Elsevier Academic Press, 2004), 1 page.
Badre, et al. "Frontal Cortex and the Discovery of Abstract Action Rules," Neuron, vol. 66, pp. 315-326, Elsevier, (Apr. 29, 2010), 12 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal modulation of visual processing in humans," Nature Neuroscience, vol. 3, No. 4, Nature America, http://neurosci.nature.com, (Apr. 2000), 5 pages.
Zyga, "A Baseball Cap That Reads Your Mind," PhysOrg.com, located at www.physorg.com/news130152277.html, (May 16, 2008), 11 pages.
Klimesch, et al., "Episodic and semantic memory: an analysis in the EEG theta and alpha band," Electroencephalography and clinical Neurophysiology, vol. 91, 1994, 27 pages.
Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.
Knight, "Contribution of human hippocampal region to novelty detection," Nature, vol. 383, www.nature.com, (Sep. 19, 1996), 4 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.
Knight, et al., "Prefrontal cortex regulates inhibition and excitation in distributed neural networks," Acta Psychologica vol. 101, pp. 159-178, Elsevier (1999), 20 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, 3-9 (Feb. 1971), 7 pages.
Lachaux et al., "Measuring Phase Synchrony in Brain Signals," Human Brain Mapping 8 (1999), 194-208, 15 pages.
Larose, Daniel T., Data Mining Methods and Models, John Wiley & Sons, Inc., 2006, 14 pages.

(56) References Cited

OTHER PUBLICATIONS

Lee et al., "What is 'neuromarketing'? A discussion and agenda for future research," International Journal of Psychophysiology, vol. 63, pp. 199-204, Elsevier (2006), 6 pages.

Lekakos, "Personalized Advertising Services Through Hybrid Recommendation Methods: The Case of Digital Interactive Television," Department of Informatics, Cyprus University, (2004), 11 pages.

Lewis et al., "Market Researchers make Increasing use of Brain Imaging," ACNR, vol. 5, No. 3, pp. 36-37, (Jul./Aug. 2005), 2 pages.

Liu, Bing, Web Data Mining: Exploring Hyperlinks, Contents, and Usage Data (Data-Centric Systems and Applications), Springer-Verlag, 2007, 643 pages.

Luck, et al., "The speed of visual attention in schizophrenia: Electrophysiological and behavioral evidence," Schizophrenia Research, pp. 174-195, Elsevier B.V. www.sciencedirect.com, (2006), 22 pages.

Makeig, et al., "Dynamic Brain Sources of Visual Evoked Responses," Science, vol. 295, www.sciencemag.org, (Jan. 25, 2002), 5 pages.

Makeig, et al., "Mining event-related brain dynamics," Trends in Cognitive Sciences, vol. 8, No. 5, (May 2004), www.sciencedirect.com, 7 pages.

Miltner, et al., "Coherence of gamma-band EEG activity as a basis for associative learning," Nature, vol. 397, www.nature.com, (Feb. 4, 1999), 3 pages.

Moran, et al. "Peak frequency in the theta and alpha bands correlates with human working memory capacity," frontiers in Human Neuroscience, vol. 4, Article 200, www.frontiersin.org, (Nov. 11, 2010), 12 pages.

Neurofocus—Neuroscientific Analysis for Audience Engagement, accessed on Jan. 8, 2010 at http://web.archive.org/web/20080621114525/www.neurofocus.com./BrandImage.htm, (2008), 2 pages.

Newell et al., "Categorical perception of familiar objects," Cognition, vol. 85, Issue 2, pp. 113-143 (Sep. 2002), 31 pages.

Nielsen, "Neuroinformatics in Functional Neuroimaging," Informatics and Mathematical Modeling, Technical University of Denmark, (Aug. 30, 2002), 241 pages.

Non-Final Office Action dated Apr. 1, 2013 of related U.S. Appl. No. 12/749,376, 23 pages.

Non-Final Office Action dated Apr. 25, 2013 of related U.S. Appl. No. 12/426,259, 16 pages.

Non-Final Office Action dated Aug. 1, 2014 of related U.S. Appl. No. 13/779,528, 38 pages.

Non-Final Office Action dated Feb. 13, 2013 of related U.S. Appl. No. 13/089,752, 11 pages.

Non-Final Office Action dated Feb. 21, 2013 of related U.S. Appl. No. 13/657,432, 16 pages.

Notice of Allowance dated Jul. 16, 2012 of related U.S. Appl. No. 11/850,650, 9 pages.

Oberman et al., "EEG evidence for minor neuron activity during the observation of human and robot actions: Toward an analysis of the human qualities of interactive robots," Neurocomputing 70 (2007) 2194-2203, 10 pages.

Padgett et al., "Categorical Perception in Facial Emotion Classification," In Proceedings of the 18th Annual Conference of the Cognitive Science Society, pp. 249-253 (1996), 5 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Paller, et al., "Validating neural correlates of familiarity," TRENDS in Cognitive Sciences, vol. 11, No. 6, www.sciencedirect.com, (May 2, 2007), 8 pages.

Palva et al., "Phase Synchrony Among Neuronal Oscillations in the Human Cortex," Journal of Neuroscience 25 (2005), 3962-3972, 11 pages.

Picton, et al., "Guidelines for using human event-related potentials to study cognition: Recording standards and publication criteria," Psychophysiology, pp. 127-152, Society for Psychophysiological Research, (2000), 26 pages.

Rizzolatti et al., "The Mirror-Neuron System," Annu. Rev. Neurosci., vol. 27, pp. 169-192, (Mar. 5, 2004), 30 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Rugg, et al., "Event-related potentials and recognition memory," TRENDS in Cognitive Sciences, vol. 11, No. 6, www.sciencedirect.com, (May 3, 2007), 7 pages.

Rugg, et al., "The ERP and cognitive psychology: conceptual issues," (Sep. 1996), 7 pages.

Sammler et al., "Music and emotion: Electrophysiological correlates of the processing of pleasant and unpleasant music," Psychophysiology, vol. 44, Blackwell Publiching Inc., 2007, 12 pages.

Schmidt et al., "Frontal brain electrical activity (EEG) distinguishes valence and intensity of musical emotions," Cognition and Emotion, vol. 15 (4), Psychology Press Ltd, 2001, 14 pages.

Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.

Soderland et al., "Customer Satisfaction and Links to Customer Profitability: An Empirical Examination of the Association Between Attitudes and Behavior," SSE/EFI Working Paper Series in Business Administration, Jan. 1999, 22 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Sullivan et al., "A brain-machine interface using dry-contact, low-noise EEG sensors," In Proceedings of the 2008 IEEE International Symposium on Circuits and Systems, (May 18, 2008), 4 pages.

Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

U.S. Appl. No. 12/426,259, filed Apr. 19, 2009, 91 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Voytek, et al., "Dynamic Neuroplasticity after Human Prefrontal Cortex Damage," Neuron 68, pp. 401-408, Elsevier Inc., (Nov. 4, 2010), 8 pages.

Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.

Voytek, et al., "Prefrontal cortex and basal ganglia contributions to visual working memory," PNAS Early Edition, www.pnas.org/cgi/doi/10.1073/pnas.1007277107, (2010), 6 pages.

Voytek, et al., "Shifts in gamma phase-amplitude coupling frequency from theta to alpha over posterior cortex during visual tasks," Frontiers in Human Neuroscience, doi: 10.3389/fnhum.2010.00191, (Oct. 19, 2010), 9 pages.

Wang, "Neurophysiological and Computational Principles of Cortical Rhythms in Cognition," Physiol Rev 90: pp. 1195-1268, American Physiological Society, www.prv.org, (2010), 75 pages.

(56) References Cited

OTHER PUBLICATIONS

Waldorff, "Distortion of ERP averages due to overlap from temporally adjacent ERPs: Analysis and correction," Psychophysiology, Society for Psychophysiological Research, Cambridge University Press (1993), 22 pages.

Woodman, et al., "Serial Deployment of Attention During Visual Search," Journal of Experimental Psychology: Human Perception and Performance, vol. 29, No. 1, pp. 121-138, American Physiological Association (2003), 18 pages.

Yamaguchi, et al., "Rapid-Prefrontal-Hippocampal Habituation to Novel Events," The Journal of Neuroscience, pp. 5356-5363, Society for Neuroscience, (Apr. 29, 2004), 8 pages.

Final Office Action dated Sep. 24, 2015 of related U.S. Appl. No. 12/426,259, 27 pages.

Klimesch, et al., "Episodic and semantic memory: an analysis in the EEG theta and alpha band," Electroencephalography and clinical Neurophysiology, vol. 91, 1994, 14 pages.

* cited by examiner

DATA COLLECTION SYSTEM FOR AGGREGATING BIOLOGICALLY BASED MEASURES IN ASYNCHRONOUS GEOGRAPHICALLY DISTRIBUTED PUBLIC ENVIRONMENTS

FIELD OF THE INVENTION

The present invention relates to systems and methods for measuring biologically and behaviorally based responses to content in targeted demographics and locations.

BACKGROUND OF THE INVENTION

There are many different kinds of audio, visual and audio-visual presentations and activities that people are exposed to every day. These presentations serve as sensory experiences that stimulate our senses and are known to result in biologically based responses that can be measured electronically and mechanically (for example, heart rate, respiration rate, blood pressure, and skin conductance).

A commonly used approach in making measurements for evaluating these presentations is that of interrogation, wherein the television/media viewer and/or Internet user and/or game player is asked to identify himself or herself as a member of the television/media audience or as an Internet user or as a game player. In connection with television viewing, this inquiry is usually done by means of an electronic prompting and data input device (for example, as in a Portable People Meter by Arbitron, Inc.) associated with a monitored receiver in a statistically selected population and monitoring site. The member identification may also include age, sex, and other demographic data. However, these non-biologically based self-report methods of measuring audience response are known to be highly error prone.

In fact, personal logs are subjective resulting in recall biases, home monitoring devices require event-recording by the person and suffer low compliance, while digital monitoring of cable and internet signals cannot identify which household member or members are in the audience nor can they evaluate the level of responsiveness by those members. Other methods of self-report offer valuable data, but are highly error prone and cannot track the moment-to moment responses to media consumption and participation in interactive activities.

In particular, with the development of the internet and its expansion into many everyday activities, people are constantly exposed to interactive media and activities. Nonetheless, the ability to measure and evaluate the user experience, effectiveness, and the usability of these interactive media has been limited. In fact, current methodologies for measuring or evaluating user experience, effectiveness, and usability of websites and other interactive internet and software media has thus far been limited to traditional self-report and eye-tracking on an individual user basis. These prior art techniques involved asking the individual user questions about the experience and evaluating where the user was looking during the interactive activity.

These prior art systems require advanced knowledge of demographic data prior to the implementation of the system. For example, in order to ensure an audience made of selected demographics and geographic regions, the audience must be prescreened to identify individuals and households within the specific geographic regions and within the specified demographic categories. Thus, the only alternative is to select individuals and households at random. However, selecting individuals and households at random does not guarantee that certain demographics and/or geographic areas are available for research.

The majority of systems acquiring biologically based signals for measuring the performance of content stimuli are laboratory-based where participants are brought in to a testing facility and their biologically-based signals are acquired using specialized equipment while watching target content. While attempts have been made to gather EEG data in home environments, compliance by the targeted audience is difficult because there is no guarantee as to whether or not the signals collected remotely are from the targeted person or another member of the household.

Accordingly, the challenges of the current methods and systems include, but are not limited to: (1) security (due to the content being provided over the internet or through a home monitoring device which then creates the possibility of an audience member recording and subsequently distributing the content); (2) carefully selected distribution mandatory (in order to reach a wide array of people and fulfill targeted demographics); (3) errors (due to the heavy reliance on self-reporting); and verification of compliance with study parameters (such as whether the data collected is from the targeted demographic); (5) associated costs with (a) lab-based methods (bringing the audience into the lab are very high) and (b) home-based audience monitoring (the costs of ensuring compliance are high), and for both (a) and (b) ensuring a geographic distribution is not easy and could compound the associated costs); and (6) determination of invalid signals is unavailable until post-processing (which requires additional steps and increases costs).

Thus, a need in the art exists for a system and method that is capable of integrating self-report and physiological data and capable of secure distribution. In addition, a need exists for an efficient and cost-effective system and method that is capable of integrating self-report and physiological data that can ensure a wide geographic distribution to an audience. Finally, a need exists for a system that is capable of providing results from a wide variety of demographic categories when monitoring unconscious biological responses and other responses to track performance of target stimuli.

SUMMARY OF THE INVENTION

The present invention is directed to a method of determining a measure of response of remotely located audiences to a target stimulus at a plurality of locations including the steps of: providing at each location at least one biologically based sensor operable to measure at least one unconscious biological response for each member of an audience; providing at each location a computer system operable to receive data representative of the at least one unconscious biological response, wherein the computer further includes a memory for storing the data; receiving at each location at least one target stimulus; exposing each member of the audience at each location to a presentation of the at least one target stimulus; obtaining a first set of data representative of the at least one unconscious biological response from the presentation for each audience member; and transmitting the first set of data to a central location for analysis.

In one embodiment, the method further includes the step of analyzing the first set of data and reporting the results. In another embodiment, the method further comprises the step of comparing the first set of data to data from a standard testing template of content stimuli.

The at least one unconscious biological response may include heart rate, galvanic skin response, respiration, and motion. In one embodiment, the at least one biologically based sensor includes a first sensor operable to measure heart rate and a second sensor operable to measure galvanic skin response.

In another embodiment, the method further includes the steps of: providing at each location at least one of a biologically based measuring device operable to measure EEG, at least one neuroimaging modality, or a combination thereof, a device operable to measure facial expression, a device operable to measure eye movement, or combination thereof, wherein the computer system is operable to receive and store data representative of EEG, at least one neuroimaging modality, facial expression, eye movement, and combinations thereof; obtaining a second set of data representative of at least one of EEG, at least one neuroimaging modality, facial expression, eye movement, or combinations thereof from the presentation for each audience member; and transmitting the second set of data to a central location for analysis.

The method may also include the step of receiving demographic information in at least one demographic category from each member of the audience. In one embodiment, the at least one demographic category comprises age, gender, race, income, and educational background. In another embodiment, the system may aggregate the demographic information for each demographic category, receive a terminal value for each demographic category, receive an alternate target stimulus, and expose an individual audience member within a certain demographic category to a presentation of the alternate target stimulus if the terminal value for the certain demographic category has been reached.

The present invention is also directed to a system for determining a measure of response of a remotely located audience to a target stimulus including: at least one biologically based sensor operable to measure at least one unconscious biological response for each member of an audience; a computer system operable to receive data representative of the at least one unconscious biological response, wherein the computer system further includes a memory capable of storing the data, wherein the system is capable of receiving at least one target stimulus, wherein the system is capable of exposing each audience member to a presentation of the target stimulus, wherein the system is capable of receiving data representative of the at least one unconscious biological response for each audience member from a plurality of locations and audiences, and wherein the system is capable of obtaining demographic information from each member of each audience in each location.

In one embodiment, the system is self-contained in a single unit. The single unit may be a kiosk, a smart phone, or a tablet. In another embodiment, the demographic information includes a plurality of categories comprising at least one of age, gender, race, income, and educational background.

The at least one unconscious biological response comprises heart rate, galvanic skin response, respiration, and motion. The system may also further include at least one biologically based measuring device operable to track eye movement, wherein the system is capable of receiving data representative of the eye movement for each audience member from a plurality of locations and audiences. In another embodiment, the system may further include at least one device operable to measure facial expressions at predetermined time intervals, wherein the system is capable of receiving data representative of the facial expressions for each audience member from a plurality of locations and audiences. In yet another embodiment, the system may also further include at least one device operable to measure EEG, at least one neuroimaging modality, or combinations thereof, wherein the system is capable of receiving data representative of the EEG, at least one neuroimaging modality, or combinations thereof for each audience member from a plurality of locations and audiences.

In still another embodiment, the system may include a plurality of biologically based sensors to measure unconscious biological responses such as heart rate, galvanic skin response, respiration, and motion, at least one biologically based measuring device operable to track eye movement, at least one device operable to measure facial expressions at predetermined time intervals, and at least one device operable to measure EEG, at least one neuroimaging modality, or combinations thereof, any of all of which may be operable depending on the particular target stimuli presented. For example, the system may include all of the sensors above, but a client may request only particular measurements for any given presentation.

The system may also be capable of receiving a capacity value for each demographic category and location for a presentation of the target stimulus, wherein the system is capable of receiving an alternate target stimulus, and wherein the system is capable of exposing an audience member to a presentation of the alternate target stimulus when the capacity value is obtained. In one embodiment, the capacity values are distributed equally for each location. In another embodiment, the system is capable of receiving target demographic density information for each location. In still another embodiment, the capacity values are allocated proportionate to the target demographic density information in the location.

The system may also be capable of reporting the data representative of the at least one unconscious biological response for each audience member from a plurality of locations and audiences and demographic data to a central location. In another aspect, the system may be operable to provide a plurality of target stimuli based on at least one of geographic location or demographic category.

BRIEF DESCRIPTION OF THE DRAWINGS

Further features and advantages of the invention can be ascertained from the following detailed description that is provided in connection with the drawings described below.

DETAILED DESCRIPTION OF THE PREFERRED EMBODIMENTS

The present invention is directed to a research method and system for measuring an audience's physical, behavioral, biological and self-report responses to a sensory stimulus and reporting the results to a central location. In particular, the invention is directed to a method and system for exposing an audience to a stimulus, measuring one or more unconscious responses of one or more persons being exposed to a sensory stimulus, presentation, or interactive activity, and reporting the results to a central location. The invention allows for screening of relevant participants using client-specified demographic-targeting criteria, in geographically dispersed environments, identifying and detecting whether or not the participants have valid signal ranges during a test, thereby eliminating over-recruits and costs. Furthermore, the invention can be used to determine whether the presentation or interactive activity is more effective in a population relative to other presentations and other populations (such as may be defined by demographic, geographic, or psychographic criterion).

The sensory stimulus, presentation, or interactive activity may include an audio, visual or audio-visual stimulus, such as a sound or sequence of sounds, a picture or a sequence of pictures including video, or a combination of one or more sounds and one or more pictures, including video. The stimulus can be pre-recorded and played back on a presentation device or system (e.g., on a television, video display, projected on a screen, such as a movie) or experienced as a live performance. The stimulus can be passive, where the audience experiences the stimulus from a stationary location (e.g., in front of a television or video screen) or the stimulus can be interactive where the audience is participating in some form with stimulus (e.g., simulated roller coaster ride, shopping experience, computer game, virtual reality experience or an interactive session via the internet).

According to one aspect of the invention, the system includes a display device, a processor, and at least one biologically based sensor operable to measure unconscious biologically based responses. Preferably, the system is operatively connected to a server allowing for data to be sent and received by the system. In one embodiment, the system is equipped to simultaneously expose content (e.g., a sensory stimulus, presentation, or interactive activity) to a plurality of audience members. The system may also be operatively connected to one or more sensors for measuring eye movement/pupil dilation. According to one aspect of the invention, the system also includes one or more self report surveys.

In one embodiment of the invention, a system that captures specific unconscious biologically based signals (such as skin conductance and heart rate), optionally with other unconscious biologically based signals (such as respiration and movement), may be built using sensors that maintain the portability of the system and thus allow the system to be deployable in various geographic locations using cost-effective equipment. Additional unconscious responses or signals may also be captured by the system at varying incremental costs. For example, eye tracking, facial coding, EEG, fMRI, PET scan, MEG and the like may be used to capture additional data in response to content.

In one embodiment, the entire system may be contained in a single unit, which beneficially allows the system to be easily and rapidly deployed to a variety of locations. For example, the system may be implemented in a kiosk and deployed to a variety of public locations including, but not limited to, shopping malls, movie theatre lobbies, hotel lobbies, airport terminals, train stations, food courts, car dealership showrooms, or other public venues. The system may also be implemented in a smart phone, tablet, or the like. The ability to distribute the system to a wide variety of locations allows for a large sample population. In addition, the ability to deploy the system to specific locations allows for the ability to reach a target audience without subjecting the audience to the burden of travelling to a lab. For example, an advertiser interested in feedback from football fans could deploy a kiosk to a football stadium instead of identifying football fans in the general population and attempting to lure the fans into a lab for testing.

In one embodiment of the invention, the system is capable of displaying content relevant to the location or independent of the location. For example, in car showrooms the content displayed and tested may be related to only new cars, and unrelated to the location of the showroom. In the alternative, content related to a specific location or relevant to the population in the specific location may be displayed and tested.

According to one aspect of the invention, the system is capable of receiving instructions and content. Thus, the system may receive specific content directly from a company/client seeking feedback on an advertisement, television show, movie, website, etc. without requiring submission of the content to the system provider and or involving delay while the system provider uploads the content for review by an audience. In addition, the system is capable of transmitting the measurements and data. Preferably, the system transmits or sends data at a predefined interval. For example, the data collected by the system may be sent on a daily basis, weekly basis, or other suitable time frame. The system may also detect "idle-times" between sessions of two participants and transfer the data to the central location. According to one embodiment, the system is programmable to alter the data collection and transmission period as desired or automatically optimize to ensure less interruption of the content-viewing on the kiosks, smart phones, tablets, or the like.

Display Device

In one embodiment of the invention, any suitable display device known in the art may be employed. Suitable display devices include, but are not limited to, televisions, LCD screens, touch screens, 3-D displays, movie screen, head-mounted displays, plasma screens, a desk-top, hand-held or wearable computer device, gaming console, home or portable music device, or any other device for the presentation of passive or interactive audio, visual or audio-visual presentation. The system could also be displayed on user devices in the location such as mobile phones and other devices that include a display. A skilled artisan would readily appreciate that other technologies may be employed that are capable of exposing an audience member to a sensory stimulus, presentation, or interactive activity.

Sensors

Responses that are based in human biology can have multiple physiologic and behavioral correlations. Thus, embodiments of the present invention may include a plurality of devices and sensors to measure the unconscious biologically based responses.

One aspect of the invention includes collecting at least one measurement by eye-tracking. The eye-tracking measures can include, but are not limited to, visual attention as estimated by gaze location, fixation duration, pupil dilation, and movement within a localized area. The system can use eye-tracking or other technology to isolate specific elements, areas or moments of interest for further analysis or processing. In accordance with one aspect of the invention, the system can track what content is being viewed, who is viewing the content (including by gender and demographic/psychographic profile), which areas or sub-areas of the content are being focused on by each individual and which measured responses of the audience correspond to the viewed content.

Another aspect of the present invention includes collecting unconscious biologically based responses by measuring galvanic skin response (GSR), heart rate, heart rate variability, brain-wave activity, respiration activity, and combinations thereof. In a preferred embodiment, at least two measures of unconscious biologically based responses are obtained by the system.

The biologically based sensors or monitoring devices for measuring the unconscious biologically based responses may include any of a number of commercially available or other sensors known in the art for measuring such responses. In accordance with one aspect of the invention, the least invasive and obtrusive sensors with the most comfortable form factor should be chosen to minimize disruption of the experience. Preferably, the sensors should allow participants to experience the presentation or test stimulus "as if" they were not being monitored at all. Suitable biologically based sensors include but are not limited to wearable devices such as "smart" garments, wrist bands, shirts, sleeves, arm bands, cameras, watches, and head-gear. Multiple combinations of sensors can be used depending on the sensory stimulus, population, and location of the monitoring. In a preferred embodiment, the biologically based sensor is an arm band.

A third aspect of the present invention includes collecting behavioral data from the participants. Behavioral type responses can include, but are not limited to, facial micro and macro-expressions, head tilt, head lean, body position, body posture, body movement, and amount of pressure applied to a computer mouse or similar input or controlling device. One or more cameras and/or pressure sensors may be used in accordance with this aspect of the invention to collect behavioral data.

Self-report type measures can include, but are not limited to, survey responses to items such as perception of the experience, perception of usability or likeability of experience, demographic data, level of personal relevance to user, attitude toward content or advertising embedded in the content, intent to purchase product, game or service, and changes in responses from before and after or pre-post testing. According to one aspect, the system includes one or more data entry device. The self-report device can be any of the well known devices for permitting an audience member to report their response to a presentation or interactive activity. Typically, self-report devices include a knob, a slider or a keypad that is operated by the audience member to indicate their level of interest in the presentation. By turning the knob, moving slider or pressing a specific button on the keypad, the audience member can indicate their level of interest in the presentation or interactive activity. Alternatively, self-report device can be a computer keyboard and/or mouse that an audience member can use to interact with the presentation. Mouse movements in association with icons or elements on the computer screen can be used to indicate levels of interest. In addition, the mouse or other input device can include sensors, such as force and pressure sensors for measuring the forces applied to the mouse by the audience members. Alternatively, keyboard keys (up arrow, down arrow, page up and page down), can used to indicate levels of interest. In addition, the user can type in responses to questions or select answers to multiple choice questions. Suitable data entry devices include, but are not limited to, a mouse, keyboards, knobs, buttons, sliders, touch screens, voice recognition technology, and variations thereof. According to one aspect, the audience member enters information manually. In the alternative, one or more administrators may enter the information for an audience member.

Computer System

Some or all of the sensor data and input data can be transferred either by wire or wirelessly to the computer system and further transferred to a data processing system. Alternatively, some or all of the sensor and input data can be transferred directly to the data processing system by wired or wireless network. The network can utilize most communication technologies, including RS-232, Ethernet, WiFi, Blue Tooth and Zigbee, for example. In addition, more than one communication technology can be used at the same time, for example, the network can included wired components (such as, Ethernet and digital cable) and wireless components (such as, WiFi, WiMAX and Blue Tooth) to connect different sensors and computer system components to the data processing system. Furthermore, the data processing system can be one computer system or a cluster, group, or network of computer systems. For example, several kiosks containing the systems may be operatively connected to one another via a network.

The computer system may also include a locating device, such as a GPS device, capable of recording and reporting the position of the system via wired or wireless connection. According to one aspect of the invention, the locating device is capable of identifying and reporting the position (direction and distance) of the system in relation to other locations, including but not limited to, towns, cities, landmarks, and other reporting systems in a network of systems.

The Presentation (or Stimuli)

The presentation may consist of a mixed sequence of content stimuli, self-report surveys (before and after the presentation of content stimuli). The presentation may include, but is not limited to, the following types of content stimuli:

1. Baseline content including a variety of standard images (modeled after the International Affective Picture System (IAPS)), standard video content to evoke a range of emotions for the audience, and optional standard web content to evoke a range of web experiences;
2. Specific content for context including television programs such as Everybody Loves Raymond that are typically aired during prime-time programming;
3. Anchoring commercials, which include standard commercials (non-target) that are inserted into multiple studies to "normalize" across different audience segments and standardize scores; and/or
4. Target content, which includes specific commercials, programs, movies, websites, and the like to be tested/studied for performance/success.

For example, in one embodiment, the target content is a television show. In another embodiment, the target content is a website or page of a website. In addition to content stimuli, the demographics of audience members may be determined through a screener or other suitable method. In this aspect, a 'pre'-survey to assess the inclination toward client branding before the target content is presented and/or a post-survey to assess the same post-presentation is also contemplated.

Geographic Consideration

In one embodiment, the system is capable of identifying its geographic location including, but not limited to, city, zip code, state, county, longitude and latitude and any specific ID that is unique to a location. This advantageously allows the client to expose various content stimuli to audiences in different geographic areas. The system may also be capable of aggregating the number of responses for a particular geographic region, or for a combination of geographic region and targeted demographics. The geographic area may be predefined, or programmable. For example, a predefined region of the south east United States may include all data from Florida, Georgia, South Carolina, North Carolina, Alabama, Tennessee, Mississippi, and Virginia. In the alternative, a client may define a region, such as a specific radius surrounding a city. The system is capable of determining whether it is located within the specified boundaries, which further refines the geographic analysis of the data collected. In one embodiment, the system aggregates the number individual audience members exposed to the stimulus in a geographic area. According to one aspect, a predefined number of audience members may be set for a particular content stimulus in a particular geographic area. In one aspect, the system may not consider audience members that have invalid signals during the presentation (in the predefined number/quota to be reached). For example, if an audience member has a "flat" skin conductance response for specific durations of the stimuli, it would be considered invalid. Similarly, if the heart rate data is above and/or below a set threshold, e.g., below 30 beats per minute (bpm) and above 190 bpm, the signal would be considered invalid. Once the predefined number has been reached, the system displays an alternate content stimulus. According to one aspect of the invention, the system is capable exposing specific content for a specific geographic region. For example, a regional advertiser may specify that an advertisement only be shown in kiosks within a specific region of the country. In addition, the system is capable of generating and sending a notification when a predetermined number of participants for a particular geographic area is reached.

Demographic Consideration

In one embodiment, the system is capable of identifying and aggregating demographic information. For example, the system may prompt a user to identify at least one of age, gender, race, employment status, education level, or other demographic category. According to one aspect, the system is capable of receiving a predefined limit or threshold value for each demographic category and aggregating responses for each demographic category. The system displays an alternate stimulus to audience members of a specific category once the predefined limit for the category has been reached. In one embodiment, the system is capable of combining one or more demographic categories. For example, the system is capable of receiving targeted demographics, such as women aged 18-34, and displaying a particular content stimulus to audience members within the targeted demographic. When a predefined number of responses for a targeted demographic have been reached, alternate stimulus content will be displayed to subsequent members of the targeted demographic. In addition, the system is capable of generating and sending a notification that a predetermined number for a particular demographic category area has been reached.

According to one embodiment, the system is capable of receiving demographic information for a particular location. For example, based on information obtained through the census or another source, the system may be able to receive information including any of the demographics discussed above. The system can allocate a threshold value for each targeted demographic category in proportion to the density of the demographic category in a specific location. In the alternative, the system can allocate the threshold number for a demographic category equally in each location. In addition, the system can receive the threshold value at any time before, during, or after interaction with an audience member.

In one aspect of the invention, the system can show different content for different targeted demographic population. Since the demographics can be distributed across various geographical regions, the system can divide the pre-defined quota of demographics across the regions. For example, as shown below in Table 1, a client may specify a specific quota for a targeted demographic.

TABLE 1

Audience Member Quota to Fill

| | Male | Female | Young | Old | Core | Non-Core | Reel | Subject-Ranges |
|---|---|---|---|---|---|---|---|---|
| Male | 30 | X | 15 | 15 | ANY | ANY | 1 | 1-45 |
| Fem | X | 30 | 15 | 15 | ANY | ANY | 2 | 30-60 |

The system would then distribute this "quota-to-fill" across different geographic locations such as in Table 2.

TABLE 2

Audience Member Quota Allocated to Each Location

| Location | Gender | Male | Female | Young | Old | Core | Non-Core | Reel | Subject-Ranges |
|---|---|---|---|---|---|---|---|---|---|
| Boston | Male | 30 | X | 15 | 15 | ANY | ANY | 1 | 1-22 |
| Boston | Fem | X | 30 | 15 | 15 | ANY | ANY | 2 | 30-45 |
| LA | Male | 30 | X | 15 | 15 | ANY | ANY | 1 | 23-45 |
| LA | Fem | X | 30 | 15 | 15 | ANY | ANY | 2 | 46-60 |

In one aspect of the invention, the quota may be pre-distributed equally (or based on capacities of the locations) across locations that can cater to the targeted demographics. In another aspect of the invention, the quota may be managed by a central server and allocated on a one-by-one basis per request.

According to one aspect of the invention, the system is capable of reporting all of the measured data (e.g., unconscious biologically based signals including, but not limited to, heart rate, skin conductance, eye-tracking, facial expressions, and EEG) for any combination of demographic category and geographic region.

Additional Features

The system is operable to report the measured unconscious biologically based responses, as well as the geographic and demographic data collected. According to one aspect, the system is operatively connected (e.g., wired or wireless) to a server. The server may be operatively connected to a centrally located processing computer that conducts an analysis of all of the data gathered and generates a report of the results. In addition, each individual system may be operatively connected to other individual systems in different locations. For example, a kiosk located in Miami may be operatively connected to a kiosk in a Fort Lauderdale.

In one embodiment, the system is operable to aggregate the data collected for each system and for an entire network of systems. In addition, the system is capable of aggregating data for each geographic area and demographic category. According to one aspect of the invention, the aggregation rate is programmable into the system. For example, the system may be set to aggregate data on a daily basis, weekly basis, or monthly basis, or immediately after each audience member test. Thus, an analysis of the data may be made over specified time periods further enhancing the ability to interpret the results.

According to one aspect of the invention, after aggregating data for a specified period, the system is capable of sending a report. The report may include demographic data including the number of audience member participants in any demographic categories that are below a set value. In one embodiment, the system is capable of generating a request for more participants in the deficient category. For example, the system may generate an audio and/or visual advertisement that is displayed to entice members of a deficient category to participate. The advertisement may be of any form including signs, text messages, print, social media, video, audio, and combinations thereof. According to one aspect, the system creates a prompt, instructing an administrator to pursue participants according to a specified need, such as a deficiency in a particular geographic area or demographic category.

In addition, the system may be equipped with the capability to generate incentives and rewards. For example, as a reward or incentive to attract an audience member, the system may be equipped with a printer or similar technology that can automatically generate a coupon, voucher, or gift card. By way of example, a system programmed to display a movie trailer may be capable of supplying vouchers for a free item from the snack bar, or discounted movie tickets. The vouchers are not limited to printed paper, but may also be emailed or electronically transmitted to an audience member. Preferably, the system is programmable to alter (type, amount, or number) the reward or incentive as desired. In one embodiment, the system may offer an audience member a choice from a variety of rewards.

Method

The present invention also directed to a method of obtaining unconscious biological response data, eye-tracking, facial coding, EEG, and other measurements in response to a stimulus. The method may be implemented through the use of the system described above, or in any suitable manner. Preferably, the method is implemented through the use of a self-contained system, such as a kiosk or smart phone.

The method includes several steps discussed in greater detail below. However, the order of performing the steps is not limiting, and the method encompasses the steps performed in any logical sequence.

Figure 1:
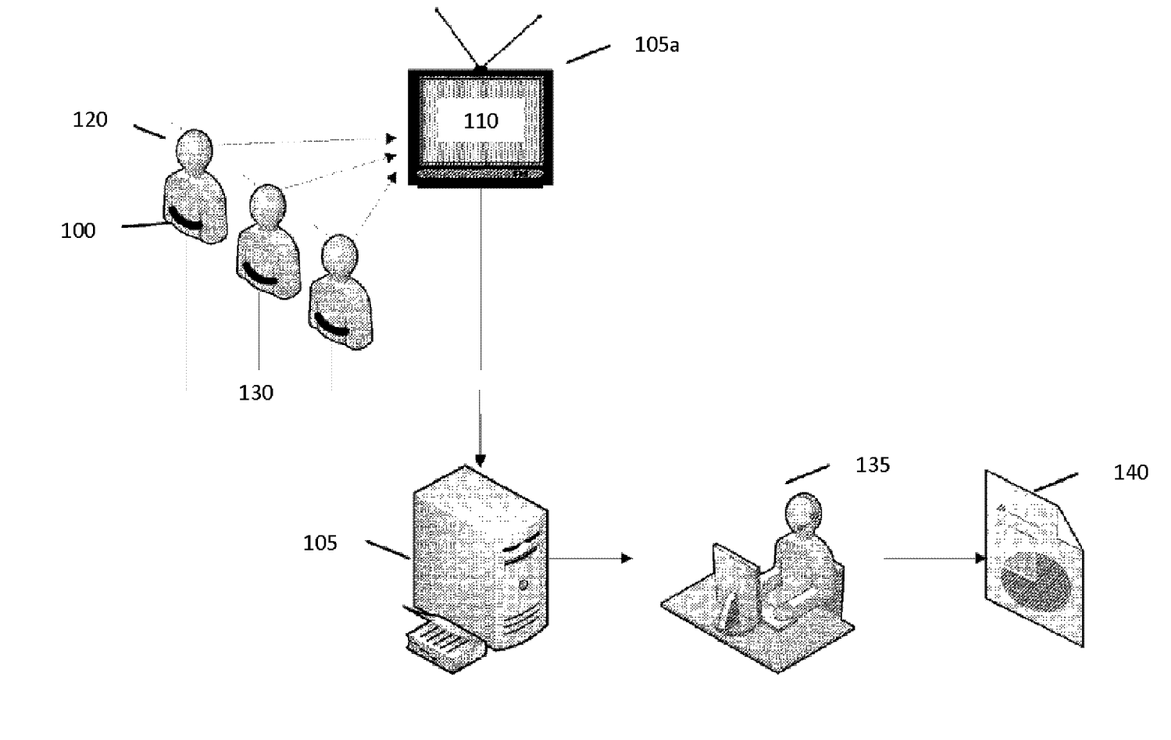
FIG. 1 is an example of a an embodiment of the method of the invention.

FIG. 1 illustrates an embodiment of the steps of the method. In step 100, at least one biologically based sensor is provided. The sensor is operable to measure at least one unconscious biological response including, but not limited to, galvanic skin response (GSR), heart rate, respiration, and movement. Preferably, at least two unconscious biologically based responses are measured. According to one aspect of the invention, the biologically based sensor comprises one or more wearable devices such as "smart" garments, wrist bands, shirts, sleeves, arm bands, cameras, watches, and head-gear. In a preferred embodiment, the biologically based sensor is unobtrusive and easily removable, such as an arm band. In accordance with one aspect of the invention, step 100 further comprises providing one or more sensors or devices capable of monitoring eye movement and/or pupil dilation. In addition, step 100 may also include providing one or more self-reporting devices including, but not limited to, mouse, keyboards, knobs, buttons, sliders, touch screens, voice recognition technology, and variations thereof.

In step 105, a computer system is provided. The computer system is operatively connected to the biologically based sensor(s) provided in step 100. In addition, the computer system is operable to receive data from the biologically based sensor(s) and any additional sensors or devices. The computer system also contains a memory for storing data collected by the system. Furthermore, the computer system is capable of sending and receiving data. Preferably, the computer system is operatively connected to a server. The connection may be wired or wireless and may employ any connection available to a skilled artisan. According to one embodiment, the computer system is operatively connected to a display device 105a. As discussed above, the display device comprises at least one of televisions, LCD screens, touch screens, 3-D displays, movie screen, head-mounted displays, plasma screens, a desk-top, hand-held or wearable computer device, gaming console, home or portable music device, or any other device for the presentation of passive or interactive audio, visual or audio-visual presentation.

According to one aspect of the invention, the computer system, biologically based sensors, display device, self reporting device, and any additional sensors are provided in a self-contained system, such as a kiosk.

The system, which preferably includes the computer system, a display device, and the biologically based sensor(s), receives at least one stimulus in step 110. As discussed above, the stimulus may comprise a sensory stimulus, presentation, or interactive activity that can include an audio, visual or audio-visual stimulus, such as a sound or sequence of sounds, a picture or a sequence of pictures including video, or a combination of one or more sounds and one or more pictures, including video. According to one embodiment, the system receives at least two stimuli. The system may combine the target content/stimuli with other "reference" and "baseline" content/stimuli to make the measurements on the target content/stimuli comparable to prior target stimuli and create scores in analysis. In fact, any of the methods for predicting audience viewing behavior and measuring user experience for interactive activities described in co-pending U.S. patent application Ser. Nos. 11/850,650, filed Sep. 5, 2007, 12/749,376, filed Mar. 29, 2010, Ser. No. 12/426,259, filed Apr. 19, 2009, and Ser. No. 13/089,752, filed Apr. 19, 2011, the entire disclosures of which are incorporated herein by reference, are contemplated for use in analyzing the data collected with the system and method of the present invention.

According to one aspect of the invention, the system receives the geographic location from a location device, such as a GPS device. In one embodiment, the system receives demographic information about individual members of the audience.

An audience member is exposed to the content stimulus in step 120. The exposure is preferably via an audio and/or visual display device operatively connected to the computer system. In one embodiment, each audience member is exposed to a stimulus individually. In the alternative, a plurality of audience members may be exposed to the stimulus simultaneously.

While the audience member is exposed to the stimulus, the sensors (including biologically based sensors, eye trackers, and self-reporting devices) obtain data in step 130, which may be stored on the computer system. The data may be transmitted to the server for analysis at a central processing facility in step 135. The data, results, and/or analysis may be included in a report in step 140.

In addition to the steps discussed above, several intermediary steps may also be included in the method. For example, according to one aspect, the system receives specific criteria related to each geographic area and demographic category, such as a desired number of participants in each area and category. In addition, the system aggregates the number of audience member participants in each category, area, and combinations thereof. When a preset number of audience member participants within a specific category, area, or combination thereof has been reached, the system offers alternative content to members of that category, area, or combination thereof. For example, the system may receive a limit of 100 participants for the category "18 to 34 year old females within 90 miles of Atlanta" for a particular movie trailer. Upon reaching the limit of 100 participants, the system will no longer display the movie trailer, and may offer a different movie trailer or other content.

In one embodiment, the method includes a step of reporting a deficiency in a specific category, area, or combination thereof. Thus, the method may also include a further step of enticing members of the deficient category, area, of combination thereof by generating an advertisement, incentive, or reward for participation. In addition, the method may also inform an administrator of a deficient category, area, of combination thereof, and prompt the administrator to recruit members of the deficient category, area, of combination thereof.

REPRESENTATIVE EXAMPLES

Example 1

The following examples are provided to illustrate an embodiment of the system and method of the present invention. The example is intended to be merely illustrative, and does not limit the scope of the claims to the embodiment presented in the example.

A kiosk is equipped with several components including biologically based sensors, cameras, computer system, touch screen, mouse, LCD display, GPS device, and wireless internet connection. All of the components are connected to the computer system. The sensors are housed within an arm band.

A movie production company desires to test a portion of two new movies in an effort to determine whether the movies will be successful, and what response the audience will have to two different version of the movie trailer. The kiosk is placed in a movie theatre lobby. The movie company is particularly interested in the response of females ages 18-34 for the first movie. The first movie clip is received by the kiosk via the wireless connection. In addition, the second movie that is targeted at men ages 18-34. A second movie clip for the second movie is received by the kiosk and stored on the computer system via the wireless connection. The movie company determines that a sample size of 100 individuals within the targeted demographic would provide sufficient test results. The kiosk receives the "100 individuals" goal for the targeted demographic for each movie clip.

In an effort to generate participation in the study, the kiosk displays an advertisement for a free popcorn voucher for audience members. Members of the public approach the kiosk and are prompted to enter their age and gender (or any screening criteria) using the touch screen (or other data entry device). The audience members are then prompted to attach the arm band and are shown the movie clip on the LCD display. Women 18-34 are shown the first movie clip and men 18-34 are shown the second movie clip. Anyone outside the targeted demographic may not be included in the testing at all, or alternatively are shown either movie clip. The unconscious brain response data is obtained by the biologically based sensors and the audience member's eye movements are tracked by the camera.

As the data is acquired for each audience member, the data is sent (immediately or deferred) via the wireless connection to a central processing server for analysis and reporting. The analysis may also be made by the computer system and subsequently reported to a central location. In addition, the computer system generates a daily report indicating the number of each demographic that has participated.

After a week, the second movie clip has been shown to over a 100 men ages 18-34. However, the first movie clip has only been shown to 70 women ages 18-34. Thus, the kiosk receives instruction to recruit women ages 18-34. In response, the kiosk generates an advertisement specifically targeting women ages 18-34.

Example 2

Several kiosks described above in Example 1 are deployed in various locations throughout the country. A movie production company desires to test a portion of two new movies in an effort to determine whether the movies will be successful, and what response the audience will have to the portion of the movies. The kiosks are placed in a movie theatre lobbies across the country.

As in the first example, members of the public approach the kiosk (or are recruited by a kiosk manager), and are prompted to enter their age, gender, and various other demographics using the touch screen. The audience members are then prompted to attach the arm band and are shown the movie clip on the LCD display.

The movie production company is particularly interested in determining interest in the movie clip from participants within a 90 mile radius of Atlanta, Ga.

The system aggregates the demographic data as well as the overall number of participants. In addition, using the location information (which may be provided by a GPS device) the computer system can calculate the distance of the kiosk from Atlanta, Ga. The system generates a report of the aggregated data and transmits the report via the wireless internet connection. In addition, the system reports the data and information related to participants that were tested at a kiosk within 90 miles of Atlanta, Ga.

The system receives a request from the movie company that the company desires at least 1000 participants from the Atlanta area. The system reports the number of participants on a daily basis. However, after a week, there have only been 500 participants from the Atlanta area. The system receives instructions to generate an advertisement in the Atlanta area for participants and generates movie vouchers as an incentive.

Example 3

Several kiosks described above in Example 1 are deployed in various locations (such as movie theatre lobbies) throughout the country. A movie production company desires to test two or more versions of a movie trailer in these locations to determine which version of the trailer will be most successful in each specific location.

As in the first and second examples, members of the public approach the kiosk (or are recruited by a kiosk manager), and are prompted to enter their age, gender, and various other demographics using the touch screen. The audience members are then prompted to attach the arm band and are shown the movie clip on the LCD display.

The system aggregates the demographic data as well as the overall number of participants. In addition, using the location information (which may be provided by a GPS device) the computer system will determine which version is successful in each location. The system generates a report of the aggregated data and transmits the report via the wireless internet connection.

Should the system receives a request from the movie company that the company desires to retest the trailer versions on specific recruits, based on income, gender, age, and the like, the system may generate an advertisement on the kiosk screen for the specific demographic that the movie company desires and retest.

A skilled artisan would recognize that the examples provided above are merely illustrative and not intended to limit the scope of the invention. For example, the system and method may be used to measure response to a wide array of content stimuli, and is not limited to movie trailers. In particular, such kiosks may be employed in other locations to test advertisements using the same general protocol.

Although the present invention has been described with reference to particular embodiments, it will be understood by those skilled in the art that the invention is capable of a variety of alternative embodiments within the spirit of the appended claims.

What is claimed is:

1. A method of determining a measure of response to a target stimulus from members of an audience remotely located at a plurality of locations, the method comprising:
   providing a processing computer including stored data, the stored data including first results from a standard testing template of content stimuli;
   providing a first portable unit at a first location, the first portable unit including:
      a first biologically based sensor to measure unconscious biological responses for a first member of an audience;
      a first processor to receive first data representative of the unconscious biological responses of the first member of the audience, the first processor including a first memory to store the first data; and
      a first display, the first biologically based sensor and the first display operatively coupled to the first processor;
   providing a second portable unit at a second location, the second portable unit including:
      a second biologically based sensor to measure unconscious biological responses for a second member of the audience;
      a second processor to receive second data representative of the unconscious biological responses of the second member of the audience, the second processor including a second memory to store the second data; and
      a second display, the second biologically based sensor and the second display operatively coupled to the second processor;
   receiving first demographic information in a demographic category from the first member of the audience;
   storing the first demographic information;
   receiving second demographic information in the demographic category from the second member of the audience;
   storing the second demographic information;
   receiving at the first location and the second location a target stimulus;
   exposing the first member of the audience to a first presentation of the target stimulus on the first display;
   exposing the second member of the audience to the first presentation on the second display;
   measuring a first unconscious biological response of the first member of the audience to the first presentation;
   forming a first set of data from the first unconscious biological response;
   storing the first set of data;
   measuring a second unconscious biological response to the first presentation for the second member of the audience;
   forming a second set of data from the second unconscious biological response;
   storing the second set of data;
   receiving at the first location and the second location an alternate target stimulus;
   exposing the first member of the audience to a second presentation of the alternate target stimulus on the first display;
   exposing the second member of the audience to the second presentation on the second display;
   measuring a third unconscious biological response of the first member of the audience to the second presentation of the alternate target stimulus;
   forming a third set of data from the third unconscious biological response;
   storing the third set of data;
   measuring a fourth unconscious biological response of the second member of the audience to the second presentation;
   forming a fourth set of data from the fourth unconscious biological response;
   storing the fourth set of data;
   transmitting the first, second, third, and fourth sets of data and the first and second demographic information to the processing computer; and
   analyzing, by executing instructions with the processing computer, the first set of data, the second set of data, the third set of data, the fourth set of data, the first demographic information, and the second demographic information to generate a report including a comparison of the target stimulus to the alternate target stimulus based on the first and second demographic information at the first and second location.

2. The method of claim 1, wherein the first, second, third, and fourth unconscious biological responses include one or more of a heart rate, a galvanic skin response, a pattern of respiration, or a motion.

3. The method of claim 2, wherein the first biologically based sensor includes a first sensor to measure the heart rate and a second sensor to measure the galvanic skin response.

4. The method of claim 1, wherein the first biologically based sensor is to measure one or more of an EEG signal, a neuroimaging modality, a facial expression, or an eye movement.

5. The method of claim 1, wherein the demographic category includes an age, a gender, a race, an income, or an educational background.

6. The method of claim 1, further including:
   obtaining third demographic data in a second demographic category from the first member of the audience;
   obtaining fourth demographic data in the second demographic category from the second member of the audience;
   aggregating the first, second, third, and fourth demographic information for the respective first and second demographic categories;
   receiving a terminal value for each of the first and second demographic categories;
   receiving a second alternate target stimulus;
   using the second alternate target stimulus for further analysis if the respective terminal value for the respective first or second demographic category has been reached.

7. A system for determining a measure of response to a target stimulus from members of an audience remotely located, the system comprising:
   a centrally located processing computer including stored data, the stored data including first results from a standard testing template of content stimuli;
   a first portable unit at a first location, the first portable unit including:
      a first biologically based sensor to measure unconscious biological responses for a first member of an audience;
      a first processor to receive first data representative of the unconscious biological responses of the first member of the audience, the first processor including a first memory to store the first data, and the first processor to transmit the first data and first demographic information collected from the first member of the audience; and
      a first display, the first display and the first biologically based sensor operatively connected to the first processor; and a second portable unit at a second location, the second portable unit including:
- a second biologically based sensor to measure unconscious biological responses for a second member of an audience;
- a second computer processor to receive second data representative of the unconscious biological responses of the second member of the audience, the second processor including a second memory to store the second data, and the second processor to transmit the second data and second demographic information collected from the second member of the audience; and
- a second display, the second display and the second biologically based sensor operatively connected to the second processor;
- the processing computer is to execute instructions to:
- expose the first member and the second member of the audience to a first presentation of the target stimulus on the respective first and second displays;
- receive, from the first remote unit, a first set of data representative of a first unconscious biological response of the first member of the audience to the target stimulus;
- receive, from the second remote unit, a second set of data representative of a second unconscious biological response of the second member of the audience to the target stimulus;
- expose the first member and the second member of the audience to a second presentation of an alternate target stimulus on the respective first and second displays;
- receive, from the first remote unit, a third set of data representative of a third unconscious biological response of the first member of the audience to the alternate target stimulus;
- receive, from the second remote unit, a fourth set of data representative of a fourth unconscious biological response of the second member of the audience to the alternate target stimulus; and
- analyze the first, second, third, and fourth sets of data, and the first and second demographic information to generate a report including a comparison of the target stimulus to the standard testing template of content stimuli.

8. The system of claim 7, the processing computer and the first and second processors operatively connected through a server.

9. The system of claim 8, wherein one or more the first or second remote unit includes a kiosk, a smart phone, or a tablet.

10. The system of claim 7, wherein the first and second demographic information includes a plurality of categories including an age, a gender, a race, an income, or an educational background.

11. The system of claim 7, wherein the first, second, third, and fourth unconscious biological responses include one or more of a heart rate, a galvanic skin response, a pattern of respiration, or a motion.

12. The system of claim 7, wherein the first biologically based measuring device is to track eye movement and the first set of data includes eye movement data.

13. The system of claim 7, wherein the first biologically based measuring device is to measure facial expressions at predetermined time intervals and the first set of data includes facial expressions data.

14. The system of claim 7, wherein the first biologically based measuring device is to measure one or more of an EEG signal or a neuroimaging modality and the first set of data includes one or more of EEG data or neuroimaging data.

15. The system of claim 7, wherein the processing computer is to execute instructions to:
- assign a capacity value to each of the first and second remote units for each demographic category and each location for the first presentation of the target stimulus and the second presentation of the alternate target stimulus; and
- expose one or more of the first member of the audience or the second member of the audience to a second alternate target stimulus on the respective first and second displays when one or more of the capacity values are obtained.

16. The system of claim 15, wherein the capacity values are distributed equally for each location.

17. The system of claim 15, wherein the processing computer is to execute instructions to transmit, to the first and second remote units, target demographic density information for the first and second locations.

18. The system of claim 17, wherein the capacity values are allocated proportionate to the target demographic density information in the first and second locations.

19. The system of claim 7, wherein the system is to provide a plurality of target stimuli based on geographic location.

* * * * *

UNITED STATES PATENT AND TRADEMARK OFFICE
CERTIFICATE OF CORRECTION

| | | |
|---|---|---|
| PATENT NO. | : 9,292,858 B2 | Page 1 of 1 |
| APPLICATION NO. | : 13/405611 | |
| DATED | : March 22, 2016 | |
| INVENTOR(S) | : Marci et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 520 days.

Signed and Sealed this
Fifth Day of July, 2016

Michelle K. Lee
*Director of the United States Patent and Trademark Office*